United States Patent [19]

Brunk et al.

[11] Patent Number: 5,474,663
[45] Date of Patent: Dec. 12, 1995

[54] BOWED FRAMED MEMBRANE, PROCESSES FOR THE PREPARATION THEREOF, AND USES THEREFOR

[75] Inventors: Donald H. Brunk, Wilmington; Charles F. Collier, Wilmington; Charles W. Robertson, Rockland, all of Del.

[73] Assignee: E. I. Du Pont de Nemours and Company, Wilmington, Del.

[21] Appl. No.: 113,538

[22] Filed: Aug. 27, 1993

[51] Int. Cl.⁶ .................. G01N 27/26; G01N 27/447
[52] U.S. Cl. .................. 204/301; 204/180.1; 204/299 R; 422/99
[58] Field of Search .................. 204/180.1, 301 R, 204/299 R; 422/99, 101, 104; 435/287, 301, 288, 299, 300; 210/232

[56] References Cited

U.S. PATENT DOCUMENTS

| | | | |
|---|---|---|---|
| 3,523,863 | 8/1970 | Juhos | 161/249 |
| 3,553,067 | 1/1971 | Dwyer et al. | 161/113 |
| 3,594,263 | 7/1971 | Dwyer et al. | 161/160 |
| 3,759,773 | 9/1973 | Dwyer et al. | 154/280 |
| 3,932,263 | 1/1976 | Brefka | 204/299 |
| 4,111,784 | 9/1978 | Dahms | 204/299 EC |
| 4,127,749 | 11/1978 | Atoji et al. | 179/110 A |
| 4,207,166 | 6/1980 | Dahms | 204/299 R |
| 4,631,120 | 12/1986 | Pohl | 204/182.8 |
| 4,631,122 | 12/1986 | Pohl | 204/299 R |
| 4,717,653 | 1/1988 | Webster, Jr. | 435/5 |
| 4,795,562 | 1/1989 | Walsh | 210/232 |
| 4,804,469 | 2/1989 | Walsh | 210/232 |
| 4,812,216 | 3/1989 | Hurd et al. | 204/182.8 |
| 4,818,360 | 4/1989 | Hurd et al. | 204/299 R |
| 4,818,701 | 4/1989 | Littlehales | 435/299 X |
| 4,828,491 | 5/1989 | Gray | 433/136 |
| 4,828,801 | 5/1989 | Lombardy et al. | 422/101 |
| 4,839,016 | 6/1989 | Anderson | 204/299 |
| 4,865,714 | 9/1989 | Sohn et al. | 204/299 |
| 4,885,697 | 12/1989 | Hubner | 364/497 |
| 4,913,791 | 4/1990 | Hurd et al. | 204/299 R |
| 4,978,507 | 12/1990 | Levin | 422/101 X |
| 5,087,558 | 2/1992 | Webster, Jr. | 435/5 |
| 5,234,559 | 8/1993 | Collier et al. | 204/182.8 |
| 5,344,543 | 9/1994 | Boquet | 204/182.8 X |

FOREIGN PATENT DOCUMENTS

| | | | |
|---|---|---|---|
| 9303359 | 2/1993 | WIPO | 422/101 |

*Primary Examiner*—John Niebling
*Assistant Examiner*—John S. Starsiak, Jr.

[57] ABSTRACT

A bowed framed membrane is disclosed for use in automated direct blot electrophoresis and subsequent membrane process steps to develop a chemiluminescent image of the resultant blot of selected fragments and to detect that image. A frame made from a thin rigid plastic plate such as polyethylene is provided with a window. A membrane covers that window and is bonded on two opposing sides only while the frame is held in a bowed condition. The membrane is maintained under tension during processing by the bowing permitting processing at the elevated temperatures used in molecular biological procedures without loss of flatness. Processes for preparing such frames and various utilities are also disclosed.

7 Claims, 2 Drawing Sheets

BOWED FRAMED MEMBRANE, PROCESSES FOR THE PREPARATION THEREOF, AND USES THEREFOR

FIELD OF THE INVENTION

This invention relates to the field of molecular biology and particularly to methods and apparatus involving the generation and analysis of electrophoretic blots from biological components such as DNA.

BACKGROUND OF THE INVENTION

Gel electrophoresis is a standard tool in biochemistry and molecular biology to separate molecular components, such as DNA, RNA or protein, either for subsequent identification or in a preparative procedure. In gel electrophoresis, the different mobility of ions under the influence of an electric field (a function of electrical charge and/or density) serves to separate molecular fragments as they move linearly in the porous medium. It is common to then transfer the separated fragments to a membrane that binds the fragments permitting further processing directed toward making an image ("blot") visible so that identification can be accomplished.

Ordinarily this transfer is done with the separated bands distributed along the body of the gel, the driving force having been removed when adequate separation has occurred. A membrane is placed on top of the gel so that the bands transfer laterally to the membrane. This is known as a Southern Blot and many variations are available.

An alternate procedure, direct blot, is described by Pohl in U.S. Pat. Nos. 4,631,120 and 4,631,122. There the bands are run to the end of the gel and transferred to a moving belt that is in contact with the end of the gel.

In U.S. Pat. No. 5,234,559 incorporated by reference herein there is disclosed an improved direct blot process and apparatus in which the bands are transferred from the end of the gel to a moving membrane that is held on a frame. The framed membrane is then subjected to the further manual or automatic processing steps required to make an image visible for identification such as the steps described in U.S. Pat. Nos. 4,717,653 and 5,087,558 by Webster, Jr. which can be followed by analysis such as that described by Hubner in U.S. Pat. No. 4,885,697. The frame is a considerable aid to the physical handling and transport of the membrane which by itself is highly flexible and incapable of self support.

Frames, and their general use in analysis and electrophoresis, are known in the art.

Hurd et al., in U.S. Pat. No. 4,812,216, 4,818,360, and U.S. Pat. No. 4,913,791, teaches a framed membrane to facilitate blotting and transfer of the membrane to and from a plurality of processing stations.

Dahms in U.S. Pat. No. 4,111,784 and 4,207,166, teaches bonding a support membrane to a bowed frame "to keep it stretched and wrinkle-free".

Dwyer et al. in U.S. Pat. No. 3,759,773, laminates a plastic base sheet to a microporous plastic membrane (the electrophoretic medium). The combination is bowed.

These and other references relating to frames are deficient in not providing means to maintain the membrane flat and taut in use and particularly so when used at a temperature that relaxes the plastic structure. The instant invention overcomes this deficiency.

SUMMARY OF THE INVENTION

There is disclosed herein apparatus for direct blot electrophoresis and automated processing and detection, comprising:

(a) frame means exhibiting elasticity under compression and having an aperture formed therethrough defining a peripheral surface within the frame means, and further wherein the frame means is bowed;

(b) a transfer membrane covering the aperture while in tension and extending beyond all portions of the peripheral surface, the membrane adapted to receive electrophoretically separated molecular fragments;

the transfer membrane being secured to the frame means on opposing portions of the peripheral surface sufficient to maintain the frame means in bowed compression and the transfer membrane in tension.

Preferably, the frame means is polystyrene and the transfer membrane is nylon 6,6.

There is also disclosed herein a process for the preparation of a substantially flat and wrinkle-free membrane for use in automated production of chemiluminescent electrophoretic images comprising:

(a) providing a frame means exhibiting elasticity under compression and having an aperture formed therethrough defining a peripheral surface within the frame means, and further wherein the frame means is initially substantially flat;

(b) covering the aperture with a transfer membrane of sufficient size to extend beyond all portions of the peripheral surface;

(c) bonding the transfer membrane to the frame means along a first portion thereof;

(d) bowing the frame means and providing a predetermined tension in the transfer membrane; and (e) bonding the transfer membrane to the frame means along a second portion thereof opposite the first portion and sufficient to maintain the frame means in bowed compression and the transfer membrane in tension.

Apparatus for the manufacture of a transfer membrane secured to a frame means in a bowed configuration is also disclosed and claimed herein.

DETAILED DESCRIPTION OF THE INVENTION

Figure 1:
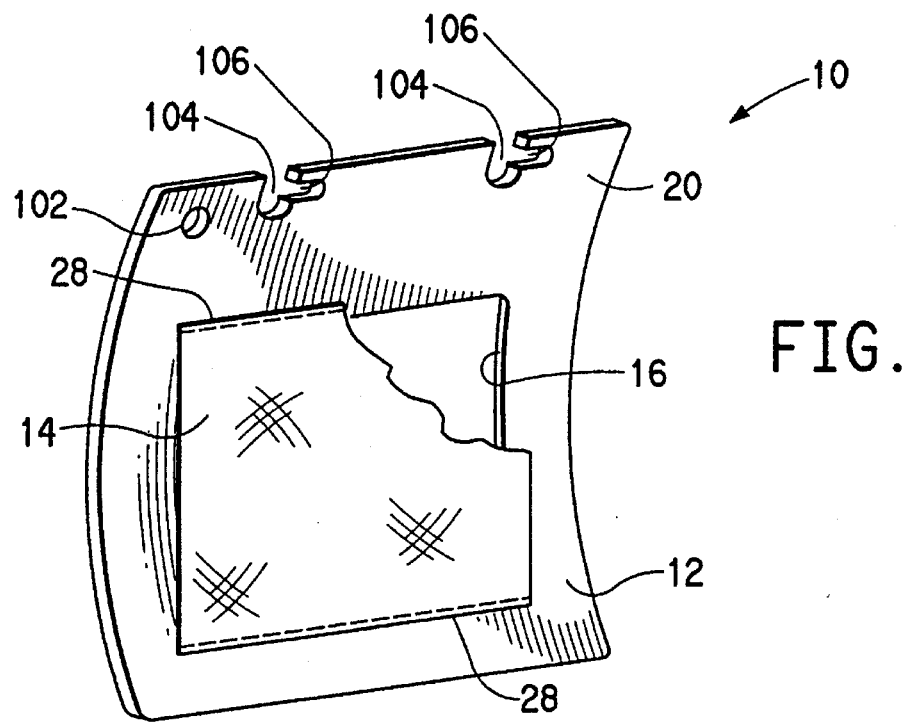
FIG. 1 is a perspective view of a bowed framed membrane according to the invention.

Refer to FIG. 1, where framed membrane unit 10 is shown in perspective. Frame 12 holds membrane 14 over window 16 with the membrane bonded to the surface of frame 12. We prefer a Biodyne B membrane available from Pall Corporation of Great Neck, N.Y. This membrane has a surface coating of nylon 6,6. It will be seen that membrane 14 is longer than window 16 and overlaps window 16 onto frame 12 on both sides. It is not bonded to these two sides. An extended portion 20 provides a convenient handling area. Extended portion 20 may be modified to suit particular automatic handling apparatus. For example, notches 104 and grooves 106 provide gripping in one such handling device and hole 102 performs a locating function.

Membrane 14 is shown in a taut and tensioned condition attached to frame 12 at lines of bonding 28 such that frame 12 is slightly bowed (this is exaggerated in the figure for clarity of exposition). For a frame fabricated from polystyrene measuring 90 mm high by 80 mm wide by 1.5 mm thick with a 55 mm high by 65 mm window wide on which a 63.5 mm by 70.0 mm membrane is mounted, the bowing at the center (the sagitta of the arc, which is maximum curvature from normal) is about 0.8 mm to 3.1 mm. Bowing is measured with a dial indicator at the center of the frame with the assembly placed concave side of the frame down on a flat surface. It should be noted that the membrane length just described is before trimming. We cut the unmounted membranes 63.5 mm long (2.5 in) and trim after bonding as close to the bond line as possible. This prevents hang-up in processing apparatus and prevents damage to the end of the gel in direct blot electrophoresis.

While a number of bonding modalities are available and known to those skilled in the art, we prefer to use ultrasonic bonding as will be described later.

The tension in membrane 14 is, of course, balanced by the moment developed by the flexed frame 12 and serves to maintain the membrane flat and unwrinkled. This is the surface configuration best suited to transferring blot patterns to the membrane 14 and to processing these patterns so that identification of the molecular fragments thereon can be made. Such a framed membrane is particularly amenable to automated and semiautomated processing. This is true because the membrane is sufficiently taut not to brush against the surrounding structure during processing and where controlled contact is needed, as in direct blot transfer, the taut and flat membrane provides uniform contact.

This bow, with the membrane taut across the concave side, keeps the membrane flat. Given adequate bowing, the membrane is tensioned by the frame even during processes at elevated temperatures where the plastic materials relax, i.e., elongate, and the membrane as a result of that elongation otherwise would go slack and wrinkle excessively. The minimum amount of bowing employed is a function of the materials used and the temperature of the process. The maximum amount of bowing is limited by the physical spacing within the processing apparatus. Good blot images are more likely to be produced by bowed framed membranes than by flat framed membranes. Bowed framed membranes are absent surface wrinkles that would induce a user to reject, and perhaps waste, what appears to be, and may indeed be, a poor component.

The method of fabrication involves employing a platen with two vacuum pads; the forward one located under an ultrasonic anvil. One end of the membrane is bonded at the forward end with both pads active. The frame is reversed and clamped near its middle. Only the forward pad is activated and the rear of the frame is pulled back and elevated while the other bond is made. Excess material beyond each of the bond lines is excised.

The bowed framed membrane 10 is particularly useful in automated apparatus for separation and transfer of molecular fragments.

Figure 2:
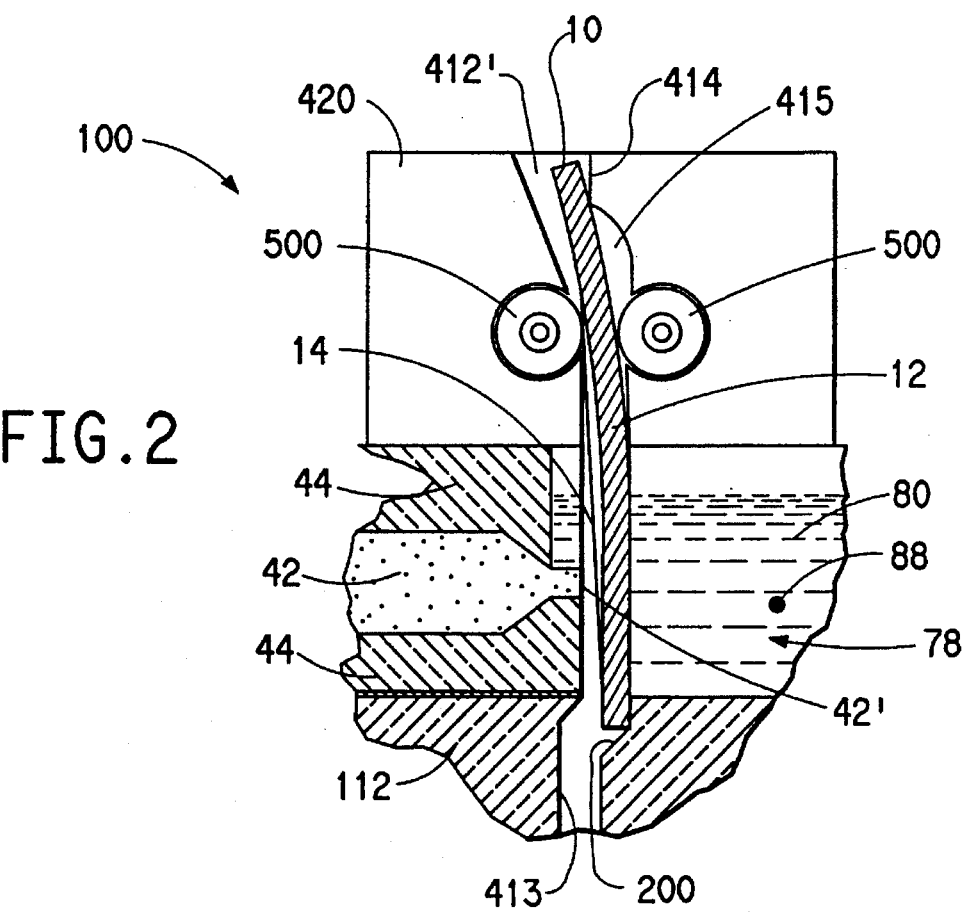
FIG. 2 is a cross-sectional view in elevation of a bowed framed membrane inserted into separation and transfer apparatus.

FIG. 2 shows a frame 12 inserted in automated apparatus 100 for electrophoretic separation of molecular fragments (gel electrophoresis) and subsequent transfer from the end of the gel to a moving membrane to form a blot which can then be further processed to develop an image readable visually or by automated means.

In FIG. 2, unit 10, as it is inserted, by hand or by automated means, into apparatus 100 is initially constrained to slide at an angle to vertical. We use an angle of about 20 degrees. Frame 12 and its attached membrane 14 moves downward during loading, driven by rubber-tired rollers 500 acting on the outside edges of frame 12, in groove 412' and is constrained by walls 200.

We prefer roller pairs at both sides and to drive all of the rollers. The angled approach allows the bonded leading edge of membrane to clear the end of gel 42 as the frame 12 strikes the far wall 200 which cams the lower end of frame 28 toward gel 42. If the bonded leading edge contacts the gel, it will very likely cause damage that would be reflected in a poorly formed blot pattern. Continued motion bends the frame to conform to the vertical portion 413 of groove 412' as it enters. Groove 412' is formed in structure 420 which is provided at opposite sides of the unit 100. The top of frame 12 then clears the end of the angled portion 414 and snaps to the far side of the widened part 415 to take up a vertical position as it is driven downward to the starting position with membrane 14 in the cavity formed by the bottom of vertical portion 413 of groove 412' in base 112. When electrophoresis is carried out in gel 42, held in holder 44, molecular fragments are driven toward the end 42' of the gel 42 under the electrical forces of electrode 88 in reservoir 78 which is filled with buffer solution 80. As the most mobile fragments, the smallest, reach end 42' rollers 500 are actuated to drive frame 12 upwards. The groove location, the roller contact, and the slight bowing of the frame 12 away from the membrane 14 cause the membrane 14 to slide under tension past the lower end of gel carrier 44 creating a desired line of tension ahead of contact with the end of gel 42. This aids in maintaining a smooth surface on to which the fragments are transferred. When the frame 12 is driven upwards towards the open top of groove 412', widened portion 415 cams the top back into the angled portion 414 for discharge.

The bowed frame unit 10 thus provides a means of attaining a controlled contact pressure between membrane 14 and the end 42' of gel 42 during separation and transfer.

Upon removal from the separation and transfer apparatus 100, unit 10 ordinarily is placed in a processing chamber in which a sequence of liquid processing steps are carried out (as is known in the technique of Southern blots modified for chemiluminescence). Typical steps which constitute this subsequent processing (the details of which are readily appreciated by those skilled in the art) are: denaturing; addition of a hybridization cocktail with hybridization at a selected temperature; washing; addition of a DNA probe; addition of a blocking cocktail; addition of an antibody-enzyme conjugate; washing; addition of assay buffer; and addition of an enzyme substrate to generate chemiluminescence.

The temperature regime during this procedure as is useful for our purposes is partly at 65° C. This is a temperature at which plastics relax. Membranes, such as the Biodyne B mentioned previously, and the polystyrene from which frame 12 is made relax. The bowing imparted to unit 10 in fabrication counteracts the elongation of the membrane as a result of the elevated temperature and the surface of the membrane remains flat as long as some residual bowing remains. This is important in automated membrane processing. We have found that we do not develop a good image of the separated material if the membrane is not flat and taut because the slack membrane adversely affects the flow pattern in the chamber. This is also important in automated detection, which follows the membrane processing. In detection, as we practice it, the framed membrane unit 10 is inserted either by hand or machine into a suitable detection module. Again, it is necessary for the surface of the membrane to be flat so that the detection device, a CCD camera in the application mentioned, focuses accurately on the surface and produces a cleanly defined image and makes even contact with the heating plate to ensure even heating. However, if there is too much bowing of the frame, the frame/membrane assembly may jam in the slot-like passages of the detection apparatus. We have found that bowing greater than 3.05 mm jams in a process involving heat as employed in our particular equipment. If a cold process is followed the maximum bow must be reduced to compensate for the absence of thermal relaxation.

Figure 3:
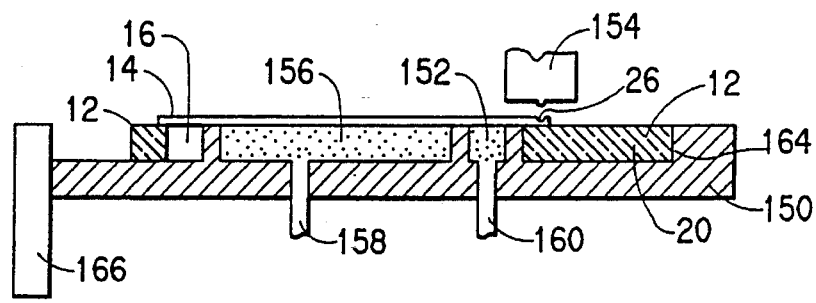
FIGS. 3, 4, and 5 are schematic cross-sectional views of process steps and apparatus for bowing a frame and bonding a membrane thereto.
Figure 4:
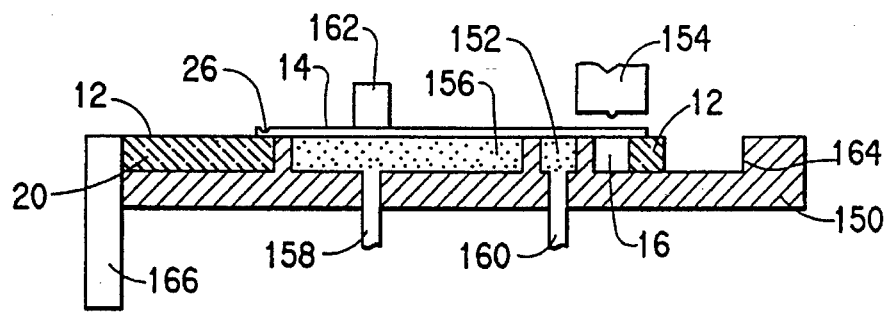
Figure 5:
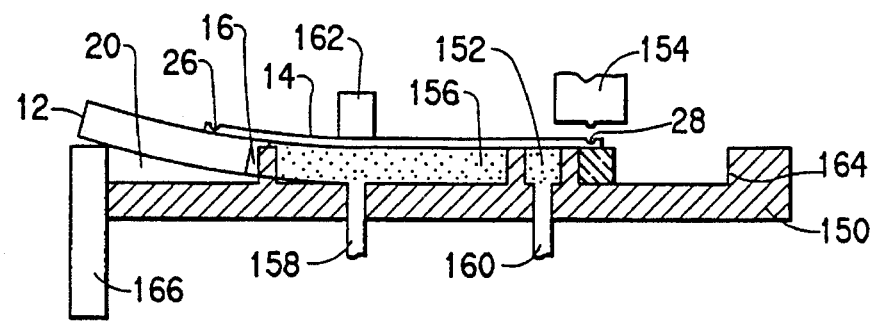

In making a bowed frame unit 10 as best seen in FIGS. 3, 4, and 5, a frame 12 with extended portion 20 forward, away from the operator or insertion device is placed on a vacuum fixture 150 that has a vacuum pad 152 beneath the anvil 154 of an ultrasonic bonder (not shown) and a vacuum pad 156 under but not quite filling the window 16 which is used as the locating element in conjunction with edge 164 of fixture 150. A membrane 14 is placed in position. Both pads are turned on by valving a source of vacuum (not shown) into pipe 158 connected to pad 156 and pipe 160 connected to pad 152. Anvil 154 is lowered, the bonder is turned on, one end of the membrane 14 fixed at line of bonding 26 to the frame 12, and the anvil 154 raised, see FIG. 3.

Having reference to FIG. 4, the vacuum is turned off and frame 12 reversed in fixture 150 aligned by the other end of window 16 and guide 166. Vacuum is turned on both pads 156 and 152 and the frame 12 is clamped by clamps 162 at both sides near the mid portion and then pad 156 is turned off leaving vacuum on pad 152, under the anvil, only. The frame is manually raised at the near side and pulled toward the operator, sliding under the clamps 162, and the edge the operator is pulling is elevated onto the top of guide 166 which bends the frame away from the taut membrane 14. See FIG. 5. The bonder is turned on and the second end of the membrane is fixed to the frame at 28. The vacuum is turned off and the clamps released permitting the frame to spring back to a very slightly bowed shape as described above and as seen in exaggerated form in FIG. 1.

This procedure is amenable to full and partial automation. We have found that good membranes are made by this apparatus and method. This evaluation is based on overall flatness of membrane, as indicated above, and bond uniformity and bond strength. We see a reduction in rejects due to non-flatness as would be expected due to stretching the wrinkles out via the tension provided by the bowed frame. We also see some improvement in bond uniformity and strength because the frame is held more snugly against the bed of the welder providing better energy transfer during ultrasonic welding.

In processing use we have found that the important parameters in frame/membrane fabrication, based on the attainment of images with good resolution and low noise, include a uniform attachment line. The membrane should be attached on two opposing sides and overlap the frame on the two unbonded sides. Excess membrane beyond the attachment line should be well trimmed. Also, bowing should be held within prescribed limits so that the minimum bow is a function of frame and membrane materials and process temperature, and the maximum bow is limited by physical spacing within the apparatus. In our system, 0.8 mm (0.030 in) minimum bow is used where the membrane is subjected to cold (room temperature) treatment only, 1.1 mm (0.045 in) minimum bow is used where the membrane is subjected to hot treatment (such as the 65° temperature described for the treatment needed for DNA hybridization), 3.1 mm maximum (0.120 in) bow is used where the membrane is used in liquid processing chambers having widths of about 2.0 mm (0.08 in) to prevent contact of the membrane with the chamber wall which may damage the image and/or cause hang-up of the frame.

Because of the many processing steps the quality of a blot, that is the final developed image, depends on a large number of factors all of which must be controlled. Differentiation of blot quality remains highly qualitative not quantitative. Failures have been identified as caused by membrane wrinkles or other physical defects, improper fluid flow, poor contact with the gel in direct-blot separation and transfer, and mechanical interference such as frame hang-up in one of the mechanisms in membrane processing or detection. Given all processing factors within prescribed limits, bowed framed membranes produce consistently good blot images. Under the same good processing conditions, a flat (unbowed) framed image also can generate an acceptable image. Moreover, unused flat framed membranes exhibit wrinkles that are objectionable in commercial service where time and money are important and any artifact that suggests even a possibility of a test failure is grounds for immediate rejection of the item.

Experience has indicated that membrane flatness (tautness) is a requisite for the intended use in automated separation and transfer, membrane processing and detection. We believe this is so for the following reasons:

Separation and transfer—preservation of the electrophoretically separated DNA fragment profile and its subsequent transfer to the membrane requires intimate and uniform contact between gel and a latitudinally and longitudinally uniform membrane. The bowed framed membrane is held flat and remains so during processing.

Membrane Processing—Uniform fluid flow in a nonturbulent sheet across both sides of the membrane is needed in all surface dependent reactions such as hybridization, blocking of unreacted sites, and washing away non-specific reagents. The bowed framed membrane has no flow-disturbing wrinkles and is not subject to flutter.

Detection—The membrane must wrap uniformly across a heating platen in the detection module for efficient heating during recordation of the chemiluminescent response. A wrinkle may inhibit uniform heating. The bowed framed membrane does not have wrinkles.

We claim:

1. Apparatus for direct blot electyrophoresis and automated processing and detection, comprising:

(a) polystyrene frame means exhibiting elasticity under compression and having an aperture formed therethrough defining a peripheral surface within said frame means, and further wherein said frame means is bowed;

(b) a transfer membrane Surface coated with nylon 6,6, said membrane covering said aperture while in tension and extending beyond all portions of said peripheral surface, said membrane adapted to receive electrophoretically separated molecular fragments;

said transfer membrane being secured to said frame means on opposing portions of said peripheral surface sufficient to maintain said frame means bowed and said transfer membrane in tension and both flat and taut.

2. The apparatus of claim 1 wherein said bow measured as maximum curvature from normal is about 0.8 mm to about 3.1 mm.

3. The apparatus of claim 2 wherein said bow is about 1.1 mm to about 3.1 mm.

4. A process for the preparation of a substantially flat and wrinkle-free membrane for use in automated production of chemiluminescent electrophoretic images comprising:

(a) providing a frame means exhibiting elasticity under compression and having an aperture formed therethrough defining a peripheral surface within said frame means, and further wherein said frame means is initially substantially flat;

(b) covering said aperture with a transfer membrane of sufficient size to extend beyond all portions of said peripheral surface;

(c) bonding said transfer membrane to said frame means along a first portion thereof;

(d) bowing said frame means and providing a predetermined tension in said transfer membrane; and (e) bonding said transfer membrane to said frame means along a second portion thereof opposite said first portion and sufficient to maintain said frame means in bowed compression and said transfer membrane in tension.

5. The method of claim 4 wherein said predetermined amount of bowing is between 0.8 mm and 3.1 mm measured as maximum curvature from normal.

6. The method of claim 4 wherein said bonds are created by ultrasonics.

7. Apparatus for the manufacture of a transfer membrane secured to a frame means in a bowed configuration, comprising:

(a) means for securing said frame means having an aperture formed therethrough defining a peripheral surface within said frame means, together with said transfer membrane so that said transfer membrane covers said aperture;

(b) means to bond said transfer membrane to first and second opposing surfaces of said peripheral surface of said frame means; and (c) means to bow said frame means and to tension said transfer membrane in between bonding of said transfer membrane to said first and second opposing surfaces of said peripheral surface.

* * * * *